(12) United States Patent
Woo et al.

(10) Patent No.: US 11,397,868 B2
(45) Date of Patent: Jul. 26, 2022

(54) FUNGAL IDENTIFICATION BY PATTERN RECOGNITION

(71) Applicant: THE UNIVERSITY OF HONG KONG, Hong Kong (HK)

(72) Inventors: Chiu Yat Patrick Woo, Hong Kong (HK); Chenyang Zhao, Hong Kong (HK); Kar Pui Susanna Lau, Hong Kong (HK); Chi Ching Tsang, Hong Kong (HK); Wang Ngai Chow, Hong Kong (HK); Siu Ming Yiu, Hong Kong (HK); Dirk Schnieders, Hong Kong (HK)

(73) Assignee: THE UNIVERSITY OF HONG KONG, Hong Kong (HK)

( * ) Notice: Subject to any disclaimer, the term of this patent is extended or adjusted under 35 U.S.C. 154(b) by 306 days.

(21) Appl. No.: 16/830,524

(22) Filed: Mar. 26, 2020

(65) Prior Publication Data
US 2021/0303845 A1 Sep. 30, 2021

(51) Int. Cl.
*G06K 9/00* (2022.01)
*G16H 70/60* (2018.01)
*G06T 7/00* (2017.01)
*G06N 20/00* (2019.01)
*G16H 50/20* (2018.01)

(52) U.S. Cl.
CPC ......... *G06K 9/00536* (2013.01); *G06N 20/00* (2019.01); *G06T 7/0012* (2013.01); *G16H 50/20* (2018.01); *G16H 70/60* (2018.01)

(58) Field of Classification Search
CPC ............ G06K 9/00536; G06K 9/6262; G06K 9/6273; G16H 50/20; G16H 70/60
USPC ........................................................ 382/128
See application file for complete search history.

(56) References Cited

U.S. PATENT DOCUMENTS

| 8,068,132 | B2 | 11/2011 | Bruno et al. | |
| 2015/0292039 | A1* | 10/2015 | Peng | C12Q 1/6895 435/6.12 |
| 2019/0250105 | A1* | 8/2019 | Mahadevan-Jansen | G01J 3/44 |
| 2021/0261646 | A1* | 8/2021 | McGinness | A61K 39/001169 |

FOREIGN PATENT DOCUMENTS

| CN | 107358193 | 11/2017 |
| CN | 109447045 | 3/2019 |

\* cited by examiner

*Primary Examiner* — Ajibola A Akinyemi
(74) *Attorney, Agent, or Firm* — Amin, Turocy & Watson, LLP

(57) ABSTRACT

A system includes a memory and a processor configured to execute computer instructions stored in the memory that when executed cause the system to perform operations. The computer instructions include a learning component that includes one or more trained models to learn pathogenic features of a given fungal species based on learning from a plurality of stored fungal species images. A fungal identifier component employs the trained models to determine pathogenic parameters of an unidentified fungal species image based on the learned pathogenic features. The fungal identifier component generates an output file that classifies the unidentified fungal species image according to the determined pathogenic parameters from the unidentified fungal species image.

23 Claims, 10 Drawing Sheets

FUNGAL IDENTIFICATION BY PATTERN RECOGNITION

TECHNICAL FIELD

This disclosure relates generally to artificial intelligence systems, and more specifically, utilizing a learning component to analyze features and parameters from a fungi training set to facilitate identification of causative fungi related to the disease.

BACKGROUND

With the advancement of medicine, there is a growing population of immunocompromised individuals such as elderlies, transplant patients, patients receiving chemotherapies, and so forth across the globe. These immunocompromised individuals are prone to opportunistic infections caused by fungi, which can vary from superficial infections of the skin and nails to highly fatal disease (e.g., aspergillosis) that frequently complicates other diseases (e.g., cancer). In contrast to bacterial and viral infections, fungal infections are often overlooked, underestimated, and understudied. The cornerstone of successful treatment of fungal infections is the isolation of the causative fungi and their accurate and timely identification. Presently, identification of fungi is mainly achieved through morphological examination, matrix-assisted laser desorption/ionization time-of-flight mass spectrometry, and gene sequencing. However, these technologies suffer from various problems such as the lack of expertise, low identification accuracy and user-friendly software as well as difficulties in extracting fungal proteins.

SUMMARY

The following presents a summary to provide a basic understanding of one or more examples of the invention. This summary is not intended to identify key or critical elements or delineate any scope of the different examples or any scope of the claims. Its sole purpose is to present concepts in a simplified form as a prelude to the more detailed description that is presented later.

According to an example, a system includes a memory and a processor configured to execute computer instructions stored in the memory that when executed cause the system to perform operations. The computer instructions include a learning component that includes one or more trained models to learn pathogenic features of a given fungal species based on learning from a plurality of stored fungal species images. A fungal identifier component employs the trained models to determine pathogenic parameters of an unidentified fungal species image based on the learned pathogenic features. The fungal identifier component generates an output file that classifies the unidentified fungal species image according to the determined pathogenic parameters from the unidentified fungal species image.

In another example, a method includes storing, by a system having a processor and a memory, a plurality of fungal species images. The method includes learning, by the system, pathogenic features of a given fungal species based on the stored fungal species images. The method includes determining, by the system, pathogenic parameters of an unidentified fungal species image based on the learned pathogenic features. The method includes classifying, by the system, the unidentified fungal species image according to the determined pathogenic parameters from the unidentified fungal species image.

In another example, a non-transitory machine-readable storage medium comprising executable instructions that, when executed by a processor cause the processor to store a plurality of fungal species images. The instructions identify pathogenic features of different fungal species based on the stored fungal species images. The instructions determine pathogenic parameters of an unidentified fungal species image based on the identified pathogenic features. The instructions classify the unidentified fungal species image according to the determined pathogenic parameters from the unidentified fungal species image.

In some examples, elements described in connection with the disclosed systems can be embodied in different forms such as a computer-implemented method, a computer program product, or another form. In another example, a website, a mobile application or other medium connects to the fungal species images and the trained networks described herein.

BRIEF DESCRIPTION OF THE DRAWINGS

Numerous example aspects, implementations, objects and advantages described herein will be apparent upon consideration of the following detailed description, taken in conjunction with the accompanying drawings, in which like reference characters refer to like parts throughout.

DETAILED DESCRIPTION

Figure 1:
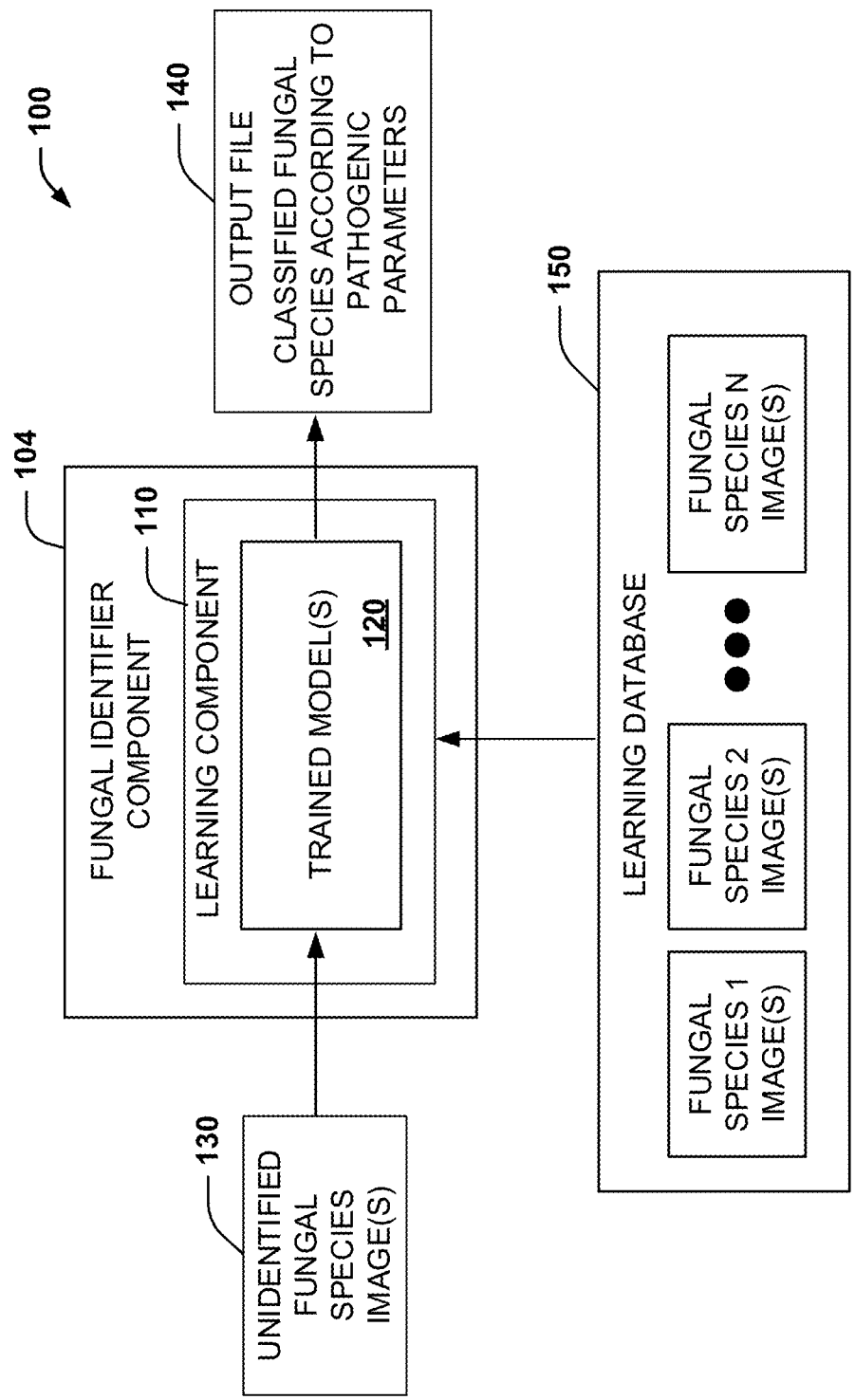
FIG. 1 illustrates a block diagram of an example, non-limiting system that includes a fungal identifier component to facilitate identification of pathogenic fungal species in accordance with one or more examples described herein.

Systems and methods are provided for analyzing and identifying pathogenic fungal species in an efficient and automated manner to facilitate diagnosis and treatment of disease caused by such species. Fungal species identification can include pattern recognition analysis of a given fungal species to select image features having pathogenic parameters that can be learned from a database of different fungal species images. Learning can include, for example, trained classifiers and/or neural network learning components that analyze various pathogenic parameters of fungal species such as size, shape, thickness, color, and other pathogenic parameters indicative of disease. Such learning includes trained probabilistic models to observe an input data set and determine a probability regarding the likelihood an unidentified input from an unknown data set from an unidentified fungal species matches one of the trained models using learned data. At least one fungal species can be identified by training the respective models from known images of fungal species. An unidentified species from a diagnostic image can be analyzed with respect to the trained models, where the trained model generates a probability output that the unidentified fungal species image correlates to the known species from the learning database. Probability thresholds can be set up that enable a model data analyzer to both determine whether the correlation is above the threshold but also report the confidence that a suitable identification of the respective fungal species has occurred.

In an example implementation, artificial intelligence (AI) along with image processing and machine/deep learning can be applied to identify clinical fungi which are difficult-to-identify using traditional phenotypic methods. This includes fungal identifier components developed using algorithms for image processing and deep learning. A learning database can be employed that includes numerous colony images of different clinical fungal species which are then used to train the respective learning components/algorithms described herein. In one example, the learning components include an accurate and reliable trained neural network (e.g., trained after multiple times of iterative training using the stored fungal images). With the image recognition and learning algorithms described herein, the fungal identifier component can identify pathogenic qualities of fungal images of unknown species. Such learning-based technological enhancement in diagnosing fungal infections can greatly improve patient management. In particular, the automation in fungal identification can facilitate conservation of manpower and thus, relieve the demand for mycological expertise in the treatment and diagnosis of fungal disease.

Various aspects of this disclosure are now described with reference to the drawings, wherein like reference numerals are used to refer to like elements throughout. In the following description, for purposes of explanation, numerous specific details are set forth in order to provide a thorough understanding of one or more aspects. It should be understood, however, that certain aspects of this disclosure may be practiced without one or more of these specific details in various examples, or with other methods, components, materials, and so forth, not explicitly mentioned herein. In other instances, well-known structures and devices are shown in block diagram form to facilitate describing one or more aspects disclosed herein.

FIG. 1 illustrates an example, non-limiting system 100 that includes a fungal identifier component 104 to facilitate identification of pathogenic fungal species in accordance with one or more examples described herein. The system 100 includes a memory and a processor (not shown) configured to execute computer instructions stored in the memory that when executed cause the system to perform operations of the system 100. The system 100 as enabled by the respective instructions described herein includes a learning component 110 that includes one or more trained models 120 to learn pathogenic features of a given fungal species based on learning from a plurality of stored fungal species images. As used herein, the term pathogenic parameters refer to substantially any feature of an image (e.g., size, shape, color) containing a fungal species that identifies the respective feature as having some quality that are characteristic to that particular pathogenic fungal species. The fungal identifier component 104 employs the trained models 120 to determine pathogenic parameters of an unidentified fungal species image 130 based on the learned pathogenic features from stored fungal species images. As shown, the fungal identifier component 104 generates an output file 140 that classifies the unidentified fungal species image 130 according to the determined pathogenic parameters from the unidentified fungal species image. Based on the classification in the output file 140 of the identified fungal species, a pathogenic fungal species infection remedy can be prescribed from such reporting and/or other measures taken (e.g., by physician and/or system) to facilitate other diagnosis and healing of the infection.

A database 150 (e.g., structured database) can be provided to store the plurality of fungal species images which are shown as Fungal Species 1 Images, Fungal Species 2 Images, and Fungal Species N Images, where N is a positive integer. The respective fungal species images in the database 150 represent images of fungal species that are known or have been previously identified as pathogenic. The database 150 can include at least one of a local memory storage, a local intranet storage across a private network, for example, and/or a distributed memory storage across a cloud or public network. In one example, the learning component 110 can be configured as a neural network. Neural network examples for identifying pathogenic fungal species are illustrated and described below with respect to FIGS. 3 through 7.

In another example, the learning component 110 can be an artificial intelligence classifier to learn the pathogenic parameters described herein. For example, the learning component 110 can learn and/or generate inferences from the fungal species images in the learning database 150 and employ such inferences to identify pathogenic parameters of the unidentified fungal species 130. The learning component 110 can employ, for example, a VGG classifier to learn and/or generate inferences with respect to fungal species identification and/or classification. Additionally or alternatively, the learning component 110 can employ other classification techniques associated with Bayesian networks, decision trees and/or probabilistic classification models. Classifiers employed by the learning component 110 can be explicitly trained (e.g., via a generic training data) as well as implicitly trained (e.g., via observing fungal behavior in response to stimuli, receiving extrinsic information). For example, with respect to VGG's that are well understood, VGG's are configured via a learning phase or training phase within a classifier constructor and feature selection module. A classifier is a function that maps an input attribute vector, x=(x1, x2, x3, x4, xn), to a confidence that the input belongs to a class—that is, f(x)=confidence(class).

Various data can be generated in the output file 140. For instance, the fungal identifier component 104 can generate data in the output file 140 such as a prediction regarding an identified fungal species type and a probability output related to a confidence of the prediction. This can include naming the unidentified fungal species 130 and can include more nuanced analysis such as the confidence that the identified species is accurate which can also include the likelihood that other potential species may be indicated. The pathogenic parameters described herein can be related to image features such as size, shape, color, and thickness of an extracted feature of the unidentified fungal species image 130. The pathogenic parameters can also be related to at least one of a refractive quality, a mass spectrometry result, and an electrical/chemical reaction of the unidentified fungal species image observed in the extracted image feature and/or data associated with the image when collected.

Figure 2:
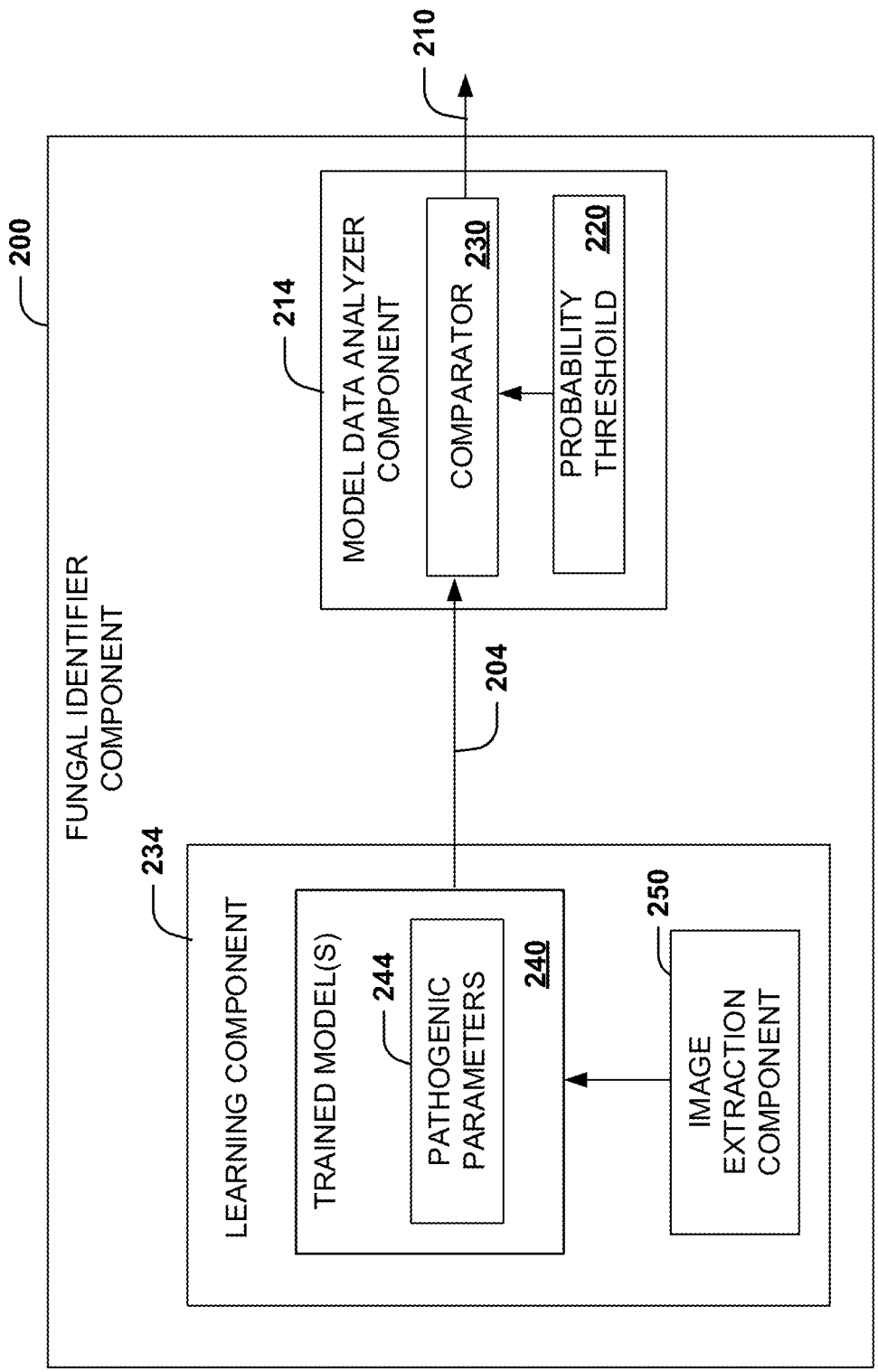
FIG. 2 illustrates a block diagram of an example of a fungal identifier component to facilitate identification of pathogenic fungal species in accordance with one or more examples described herein.

FIG. 2 illustrates an example of a fungal identifier component 200 to facilitate identification of pathogenic fungal species in accordance with one or more examples described herein. The fungal identifier component 200 generates a prediction 204 regarding an identified fungal species type and a probability output 210 related to a confidence of the prediction. A model data analyzer component 214 compares the probability output 204 to a probability threshold 220 via comparator 100 to generate the probability output 210 based on the prediction 204 exceeding the probability threshold.

A learning component 104 employs one or more trained models 240 to generate the prediction 204 regarding identification of a pathogenic fungal species. As noted previously, the learning component can include substantially any form of artificial intelligence learning such as for example, neural network learning described further below and classifier learning in another example. As shown, the trained models can include pathogenic parameters 244 which are employed as inputs to the learning functions such as neural network neurons described below. Such pathogenic parameters 244 can include image feature size, shape, color, refraction qualities, density, and so forth as previously described. Before an unknown fungal species image can be analyzed by the learning component 104, an image extraction component 250 is employed to extract image features from the respective fungal species image that are then analyzed for pathogenic qualities as described herein.

Figure 3:
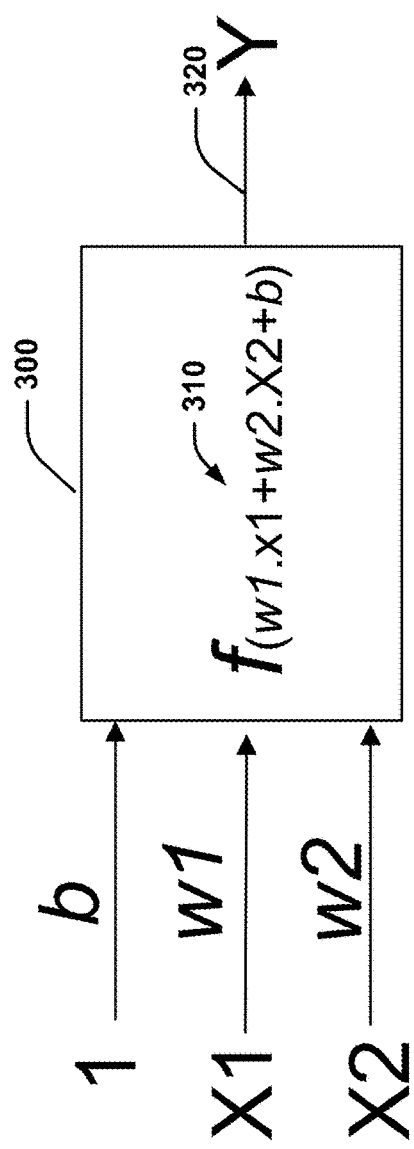
FIG. 3 illustrates an example of a neural network neuron executing an activation function to facilitate identification of pathogenic fungal species in accordance with one or more examples described herein.
Figure 4:
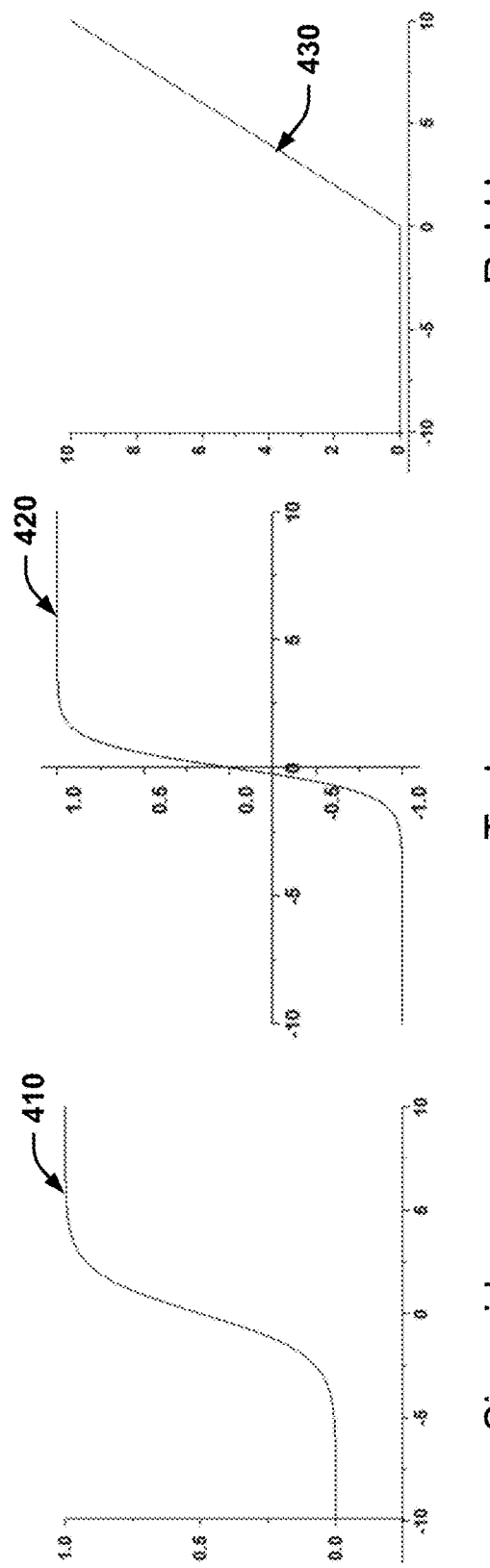
FIG. 4 illustrates activation function examples for a neural network to facilitate identification of pathogenic fungal species in accordance with one or more examples described herein.

FIG. 3 illustrates an example of a neural network neuron 300 executing an activation function 310 to facilitate identification of pathogenic fungal species in accordance with one or more examples described herein. In this example, a neural network can be implemented as at least one neuron 300 that executes an activation function 310, where the neuron receives weighted inputs X1 and X2 related to image variables (e.g., pathogenic parameters) from the stored fungal species images and generates an output that indicates learned patterns from the respective image variables. The neuron 300 takes numerical inputs X1 and X2 and has weights w1 and w2 associated with those inputs. Additionally, there is another input 1 with weight b (referred to as Bias) associated with it. The output Y at 320 from the neuron 300 is computed as shown in FIG. 4 below via example activation functions. The function f is non-linear and is called the activation function. An example purpose of the activation function is to introduce non-linearity into the output of the neuron 300.

FIG. 4 illustrates activation function examples for a neural network to facilitate identification of pathogenic fungal species in accordance with one or more examples described herein. At 410, a Sigmoid: takes a real-valued input and squashes it to range between 0 and 1. At 420, a tan h: takes a real-valued input and squashes it to the range [−1, 1]. At 430, a ReLU: ReLU stands for Rectified Linear Unit. It takes a real-valued input and thresholds it at zero (e.g., replaces negative values with zero). Examples of a Sigmoid, tan h, and ReLU are shown respectively below in Equations 1, 2, and 3:

$$\sigma(X) = \frac{1}{1 + e^{-x}} \qquad \text{Equation 1}$$

$$\tanh(X) = 2\sigma(2X) - 1 \qquad \text{Equation 2}$$

$$f(X) = \max(0, X) \qquad \text{Equation 3}$$

Figure 5:
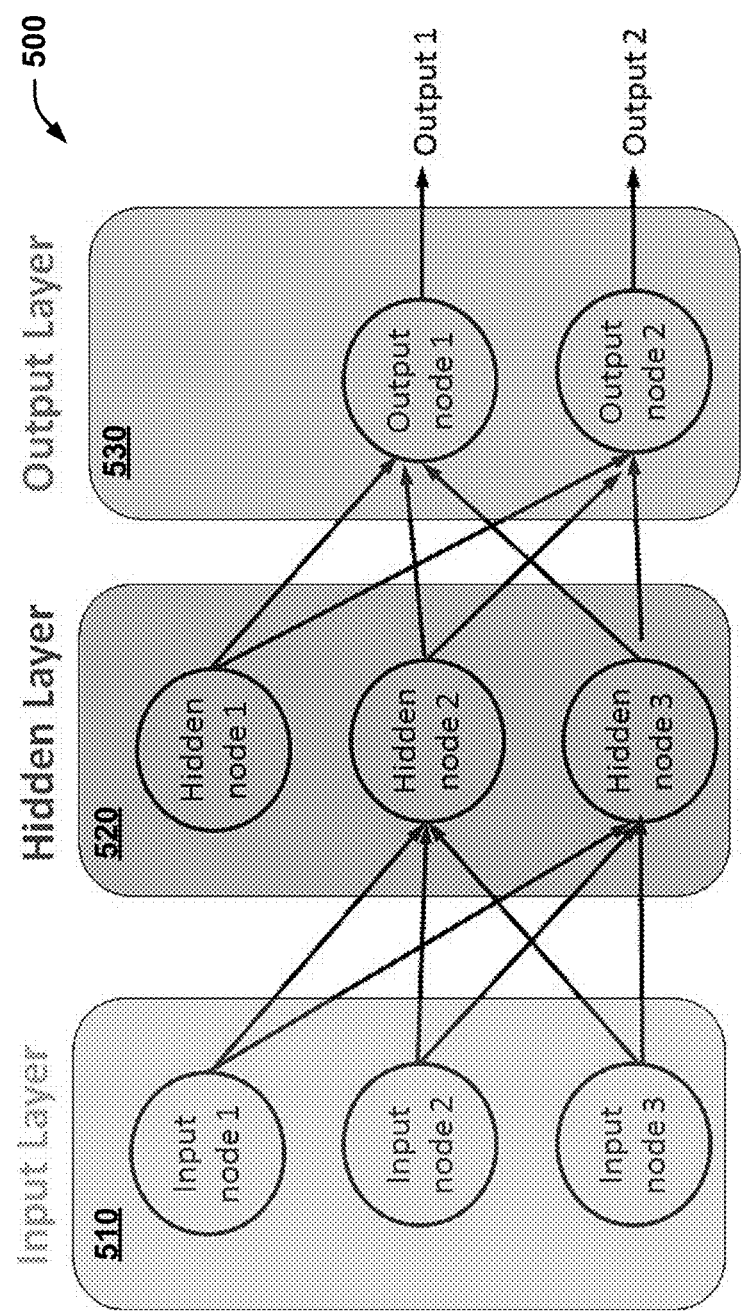
FIG. 5 illustrates an example neural network example having a probability output to facilitate identification of pathogenic fungal species in accordance with one or more examples described herein.
Figure 6:
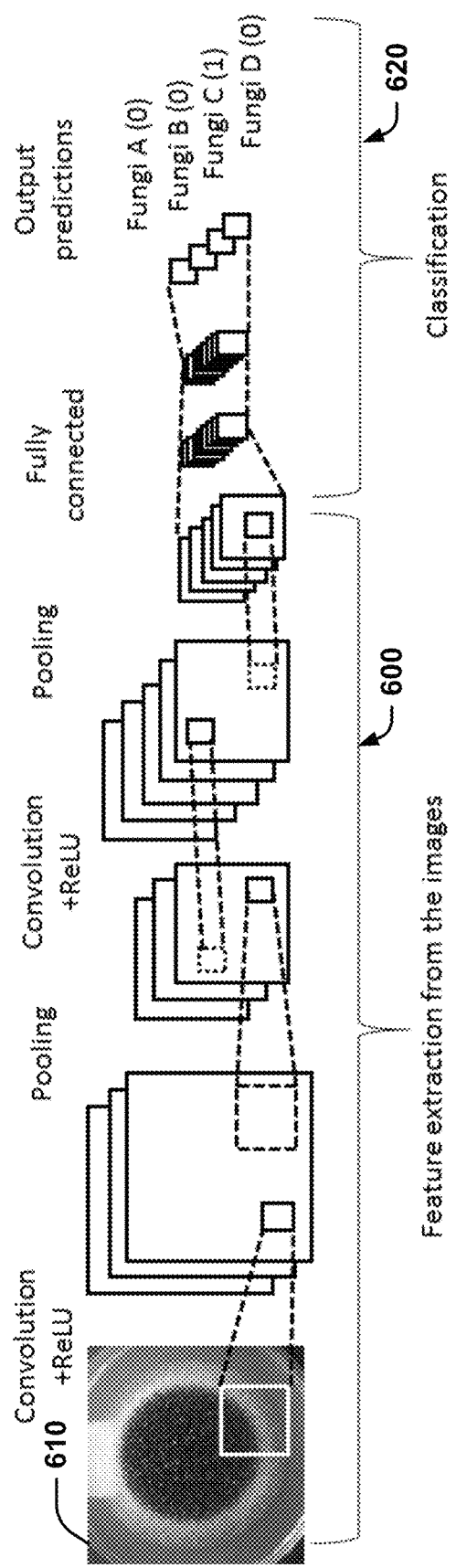
FIG. 6 illustrates an example of image extraction and classification to facilitate identification of pathogenic fungal species in accordance with one or more examples described herein.

FIG. 5 illustrates an example of a neural network 500 having a probability output to facilitate identification of pathogenic fungal species in accordance with one or more examples described herein. In this example, the neural network 500 can include an input layer having one or more input nodes to receive input data relating to fungal images. A hidden layer 520 (or layers) incorporates is connected to various learning paths from the input layer 510. An output layer 530 receives data that has been processed by the hidden layer 520 and generates one or more prediction outputs shown as Output 1 and Output 2 in this example. During the learning phase of the neural network 500, input weights applied at the input layer 510 and further processed at the hidden layer 520 can be adjusted according to their relevance in predicting the output of the network. Such weight adjustments can be determined according to back propagation and gradient algorithms to improve neural network prediction performance for pathogenic detection FIG. 6 illustrates an example of image extraction and classification to facilitate identification of pathogenic fungal species in accordance with one or more examples described herein. At 600, feature extraction is employed to extract fungal features from a respective image 610, wherein the neural network is employed to classify the extracted fungal features at 620. The processes shown at 600 and 620 can be enabled as part of convolution neural network (CNN). Image classification is the process of taking an input (e.g., fungal species image) and outputting a class (e.g., "fungus type 1") or a probability that the input is a particular class (e.g., "there's a 90% probability that this input is a fungus type 1"). The image 610 is processed according to various CNN stages that include Convolutional layers, ReLU layers, Pooling layers, and a Fully connected layer, for example. CNNs have an input layer, and output layer, and hidden layers. The hidden layers usually consist of convolutional layers, ReLU layers, pooling layers, and fully connected layers.

Convolutional layers apply a convolution operation to the input. This passes the information on to the next layer. Pooling combines the outputs of clusters of neurons into a single neuron in the next layer. Fully connected layers connect respective neurons in one layer to respective neurons in the next layer. In a convolutional layer, neurons receive input from a subarea of the previous layer. In a fully connected layer, each neuron receives input from each element of the previous layer. A CNN works by extracting features from images. This mitigates the need for manual feature extraction. Thus, the features are not trained but learned while the network trains on a set of images. This provides deep learning models that are very accurate for computer vision tasks. Also, CNNs learn feature detection through tens or hundreds of hidden layers in some examples, where each layer increases the complexity of the learned features.

In general, a CNN starts with an input image at 910 and applies many different filters to it to create a feature map during the process 900. The process 900 applies an ReLU function to increase non-linearity and applies a pooling layer to each feature map. This includes flattening the pooled images into a long vector and inputs the vector into a fully connected artificial neural network at 910. The CNN processes the features through the network. The final fully connected layer provides the "voting" of the classes to determine fungal species. The CNN trains through forward propagation and backpropagation for a plurality of epochs. This repeats until a well-defined neural network is operating with trained weights and feature detectors.

Figure 7:
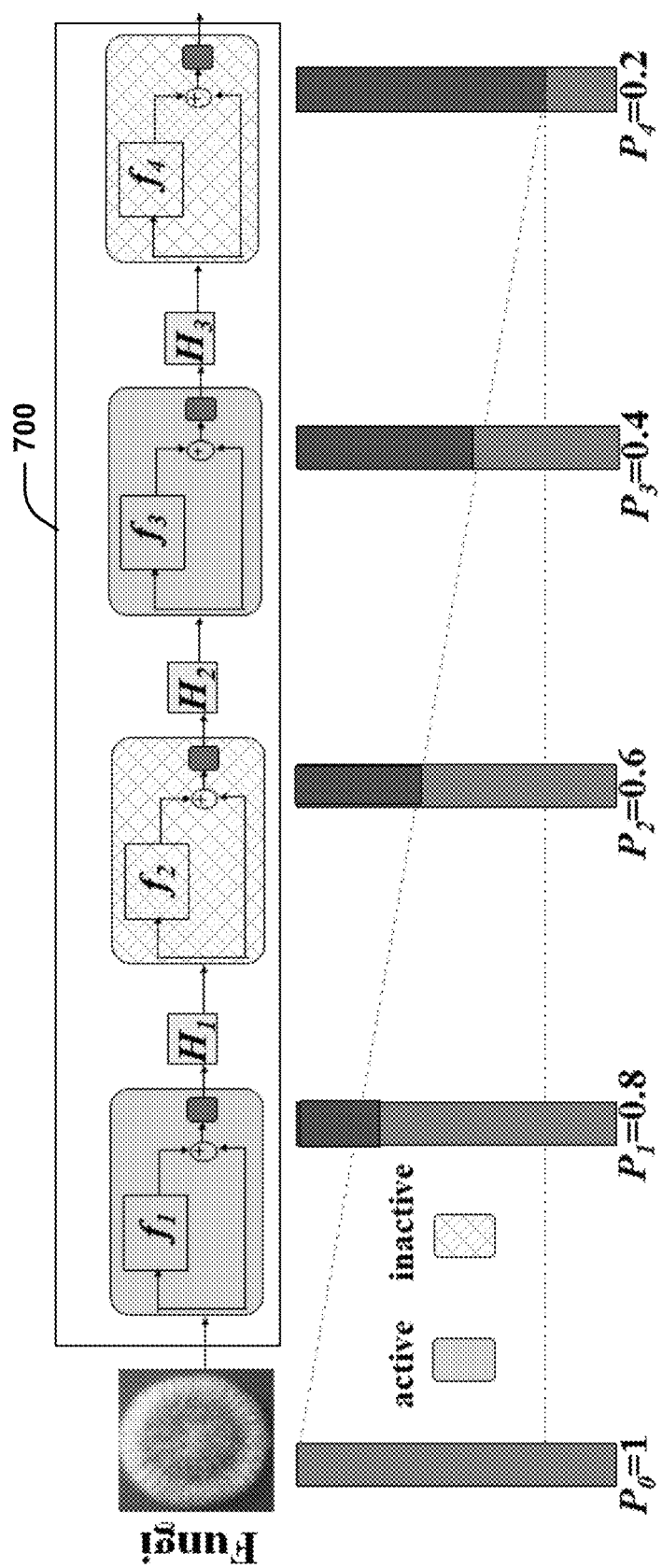
FIG. 7 illustrates an example of a layer survival probability component to facilitate network training efficiency in accordance with one or more examples described herein.

FIG. 7 illustrates an example of a layer survival probability component 700 to facilitate network training efficiency in accordance with one or more examples described herein. Current network structures can involve long training and recognition times. The systems and methods described herein reduces training and recognition time by randomly discarding some layers of the neural network during training but using the full network for testing. A hyper-parameter survival probability can be added to the neural network transmission as shown in FIG. 7, where Hi denotes the output of the ith layer, fi refers to a typical convolutional transformation from layer i−1 to layer I and Pi denotes the survival probability of ith layer, obtained as shown for example, in Equation 4:

$$p_i = 1 - \frac{i}{N}(1 - p_N)$$ Equation 4

Where N is the number of total network layers, pN denotes the constant survival probability in the last layer, set to be 0.3 in this example. Pattern image is as the input layer, the layer transmission principle follows a residual neural network (ResNet), for example. The term Pi influences whether its layer has the contribution. The output can be obtained, for example, by Equation 5:

$$H_i = \text{ReLu}(\alpha(p_i)f_i(H_{i-1}) + id(H_{i-1}))$$ Equation 5:

Where ReLu is the network activation function, id(.) denotes the identity transformation. The random chosen layers improve the transmission efficiency and reduces the residual error, but still provide the training depth.

Figure 8:
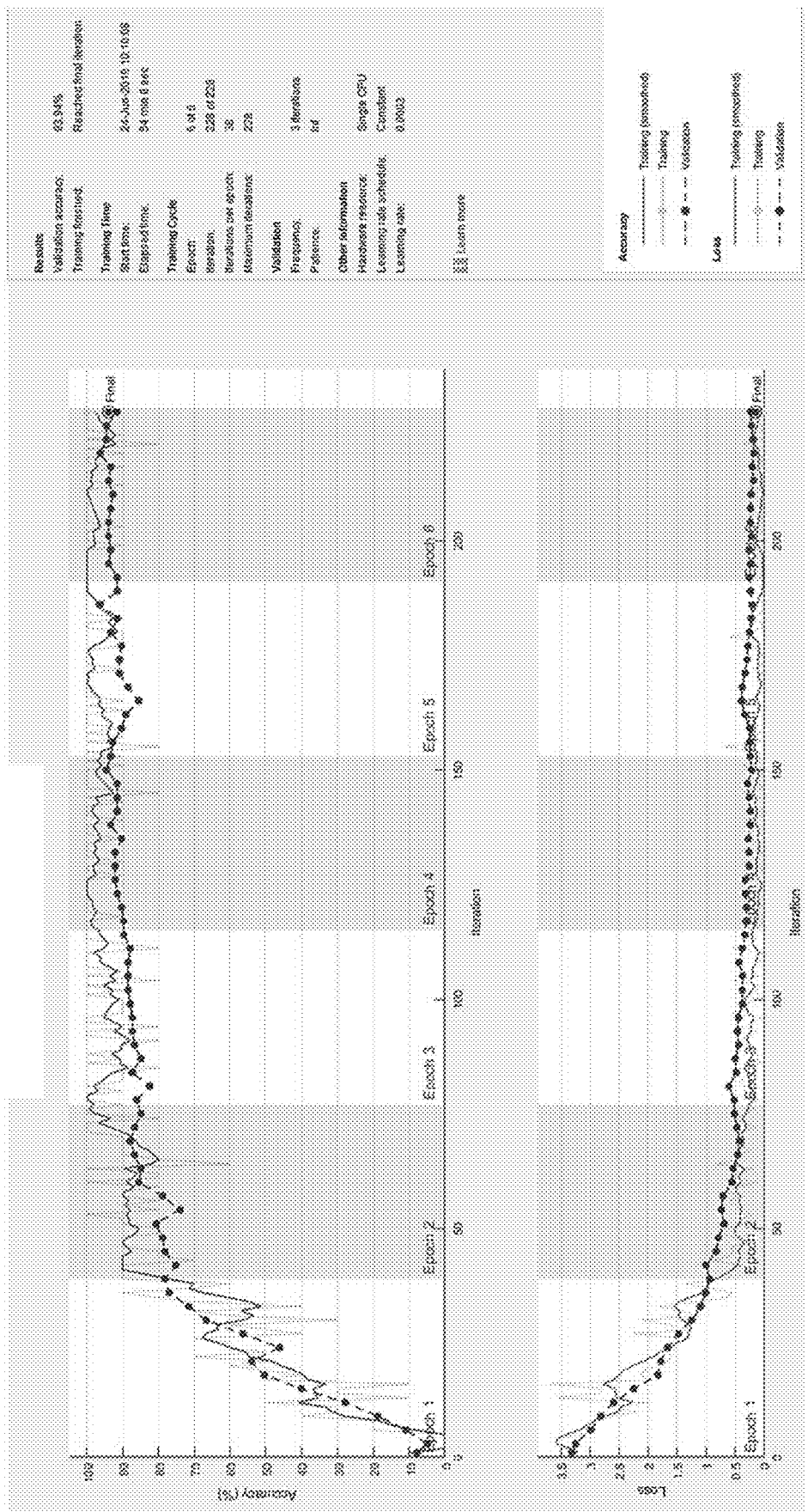
FIG. 8 illustrates example training and validation curves to facilitate identification of pathogenic fungal species in accordance with one or more examples described herein.

FIG. 8 illustrates example training and validation curves to facilitate identification of pathogenic fungal species in accordance with one or more examples described herein. In these examples, top graphs in the respective Figures represent algorithm accuracy on the vertical axis as executed over a number of iterations represented on the horizontal axis. The bottom curves of the respective Figures represent algorithm loss on the vertical axis as executed over a number of iterations represented on the horizontal axis. A total of 19 different fungal species were represented within 570 test images. As shown in FIG. 8, algorithm prediction accuracy exceeds about 90% and loss drops below about 0.01 after about 50 iterations.

Figure 9:
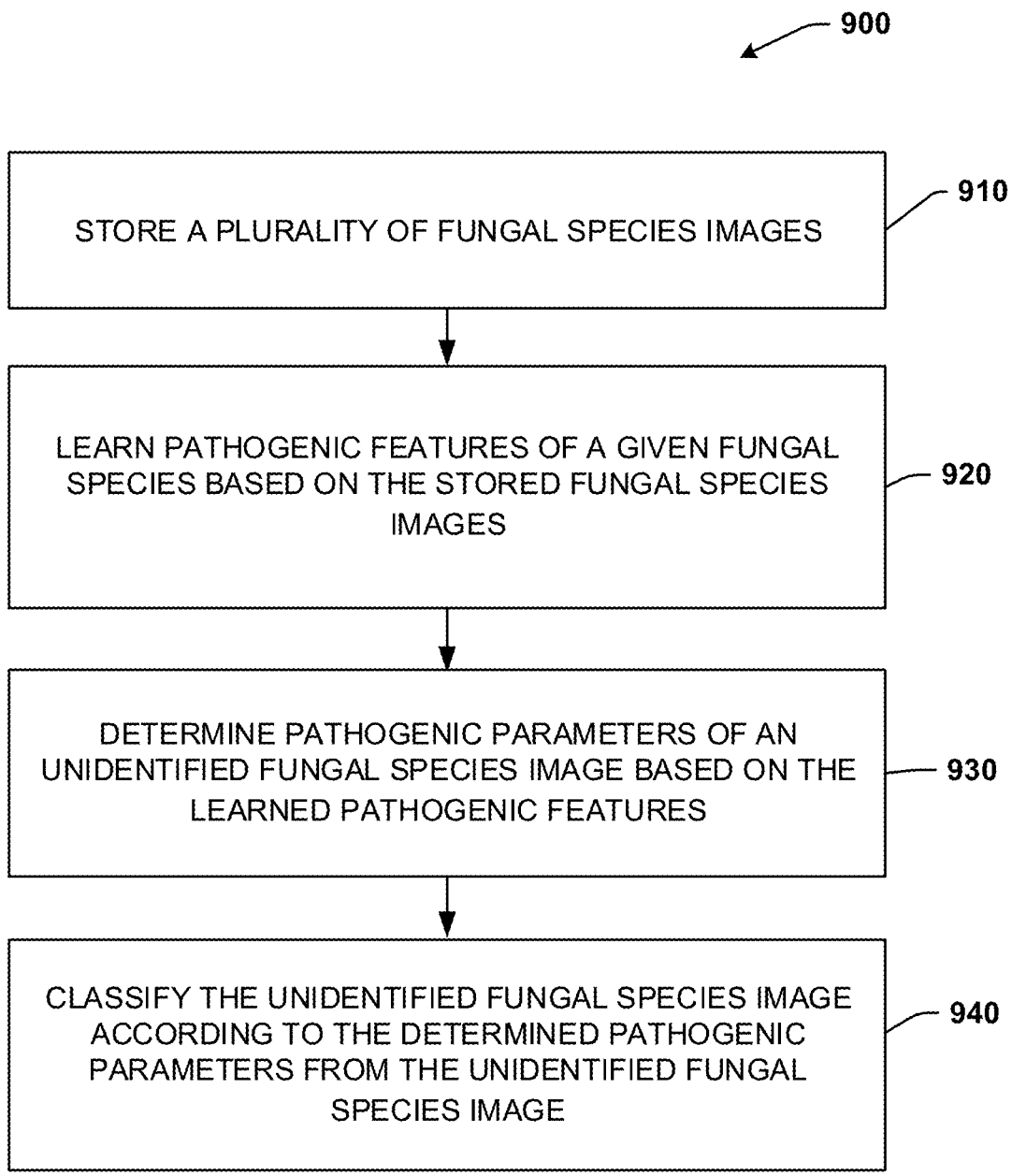
FIG. 9 illustrates a flow diagram of an example, non-limiting method to facilitate identification of pathogenic fungal species in accordance with one or more examples described herein.

FIG. 9 illustrates a computer-implemented methodology via flow diagram 900 in accordance with the disclosed subject matter. For simplicity of explanation, the methodology is depicted and described as a series of acts. It is to be understood and appreciated that the subject methods are not limited by the acts illustrated and/or by the order of acts, for example acts can occur in various orders and/or concurrently, and with other acts not presented and described herein. Furthermore, not all illustrated acts may be employed to implement the methodology in accordance with the disclosed subject matter. In addition, those skilled in the art will understand and appreciate that the methodology could alternatively be represented as a series of interrelated states via a state diagram or events. Additionally, it should be further appreciated that the methodology disclosed hereinafter and throughout this specification are capable of being stored on an article of manufacture to facilitate transporting and transferring such methodologies to computers. The term article of manufacture, as used herein, is intended to encompass a computer program accessible from any suitable computer/machine-readable device and/or storage media.

FIG. 9 illustrates an example method 900 to facilitate identification of pathogenic fungal species in accordance with one or more examples described herein. At 910, the method 900 includes storing, by a system having a processor and a memory, a plurality of fungal species images. At 920, the method 900 includes learning, by the system, pathogenic features of a given fungal species based on the stored fungal species images. At 9100, the method 900 includes determining, by the system, pathogenic parameters of an unidentified fungal species image based on the learned pathogenic features. At 940, the method 900 includes classifying, by the system, the unidentified fungal species image according to the determined pathogenic parameters from the unidentified fungal species image.

Although not shown, the method 900 can also include that the learning includes learning from at least one of a neural network and an artificial intelligence classifier to learn the pathogenic parameters. The neural network can be implemented as at least one neuron that executes an activation function, where the neuron receives weighted inputs related to image variables from the stored fungal species images and generates an output that indicates learned patterns from the respective image variables. In one example, the neural network can be implemented as a feed-forward network of neurons and output error terms are back propagated across the network to adjust input weighting terms to facilitate prediction accuracy of the network. The method 900 can also include extracting fungal features from a respective image and classifying the extracted fungal features. This can include employing convolution to extract the fungal features, generating a rectified feature map representing convolved features, and generating rectified values having negative feature values set at about zero. The method 900 can also include generating a prediction regarding an identified fungal species type and generating a probability output related to a confidence of the prediction.

In another example, the method 900 can include pre-processing of the fungi images that can include, for example, image cropping, feature detection, matching, rendering and so forth that can also include related image processing algorithms. Also, optimization of the learning process can be provided such as reducing learning time and recognition time of the neural network such as previously described above with respect to FIG. 7. The optimization can include for example, optimization of neural network transmission parameters such as described above with respect to FIG. 7.

Figure 10:
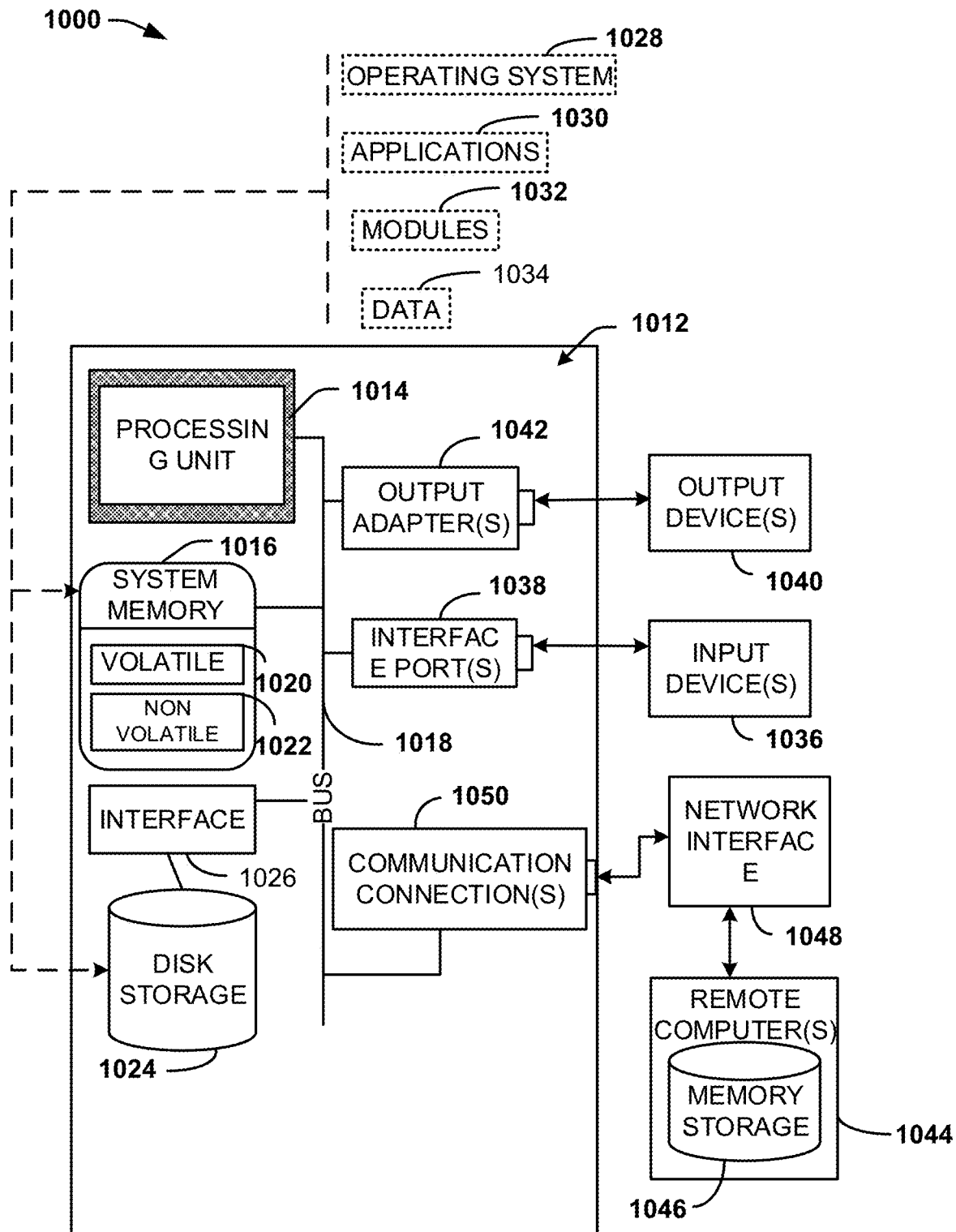
FIG. 10 is a schematic block diagram illustrating a suitable operating environment example to facilitate identification of pathogenic fungal species in accordance with one or more examples described herein.
Figure 11:
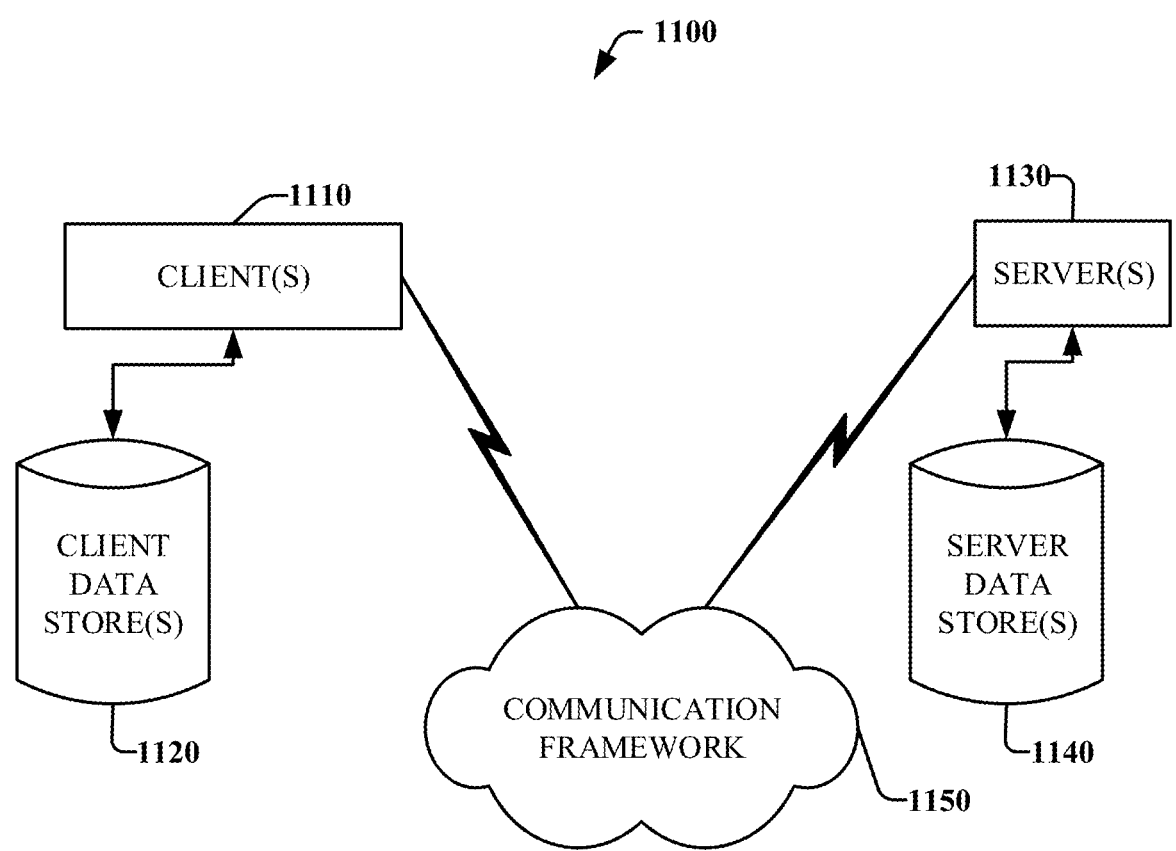
FIG. 11 is a schematic block diagram of an example-computing environment to facilitate identification of pathogenic fungal species in accordance with one or more examples described herein.

In order to provide a context for the various examples of the disclosed subject matter, FIGS. 10 and 11 as well as the following discussion are intended to provide a brief, general description of a suitable environment in which the various examples of the disclosed subject matter may be implemented.

FIG. 10 is a schematic block diagram illustrating a suitable operating environment example to facilitate storing transaction data in a blockchain in accordance with one or more examples described herein. With reference to FIG. 10, a suitable environment 1000 for implementing various aspects of this disclosure includes a computer 1012. The computer 1012 includes a processing unit 1014, a system memory 1016, and a system bus 1018. The system bus 1018 couples system components including, but not limited to, the system memory 1016 to the processing unit 1014. The processing unit 1014 can be any of various available suitable processors. Dual microprocessors and other multiprocessor architectures also can be employed as the processing unit 1014.

The system bus 1018 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1016 includes volatile memory 1020 and nonvolatile memory 1022. The basic input/output system (BIOS), containing the basic routines to transfer information between elements within the computer 1012, such as during start-up, is stored in nonvolatile memory 1022. By way of illustration, and not limitation, nonvolatile memory 1022 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1020 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1012 also includes removable/non-removable, volatile/non-volatile computer storage media. FIG. 10 illustrates, for example, a disk storage 1024. Disk storage 1024 includes, but is not limited to, devices like a magnetic disk drive, floppy disk drive, tape drive, Jaz drive, Zip drive, LS-100 drive, flash memory card, or memory stick. The disk storage 1024 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1024 to the system bus 1018, a removable or non-removable interface is typically used, such as interface 1026.

FIG. 10 also depicts software that acts as an intermediary between users and the basic computer resources described in the suitable operating environment 1000. Such software includes, for example, an operating system 1028. Operating system 1028, which can be stored on disk storage 1024, acts to control and allocate resources of the computer system 1012. System applications 1030 take advantage of the management of resources by operating system 1028 through program modules 1032 and program data 1034, e.g., stored either in system memory 1016 or on disk storage 1024. It is to be appreciated that this disclosure can be implemented with various operating systems or combinations of operating systems.

A user enters commands or information into the computer 1012 through input device(s) 1036. Input devices 1036 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1014 through the system bus 1018 via interface port(s) 1038. Interface port(s) 1038 include, for example, a serial port, a parallel port, a game port, and a universal serial bus (USB). Output device(s) 1040 use some of the same type of ports as input device(s) 1036. Thus, for example, a USB port may be used to provide input to computer 1012, and to output information from computer 1012 to an output device 1040. Output adapter 1042 is provided to illustrate that there are some output devices 1040 like monitors, speakers, and printers, among other output devices 1040, which require special adapters. The output adapters 1042 include, by way of illustration and not limitation, video and sound cards that provide a means of connection between the output device 1040 and the system bus 1018. It should be noted that other devices and/or systems of devices provide both input and output capabilities such as remote computer(s) 1044.

Computer 1012 can operate in a networked environment using logical connections to one or more remote computers, such as remote computer(s) 1044. The remote computer(s) 1044 can be a personal computer, a server, a router, a network PC, a workstation, a microprocessor-based appliance, a peer device or other common network node and the like, and typically includes many or all of the elements described relative to computer 1012. For purposes of brevity, only a memory storage device 1046 is illustrated with remote computer(s) 1044. Remote computer(s) 1044 is logically connected to computer 1012 through a network interface 1048 and then physically connected via communication connection 1050. Network interface 1048 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1050 refers to the hardware/software employed to connect the network interface 1048 to the bus 1018. While communication connection 1050 is shown for illustrative clarity inside computer 1012, it can also be external to computer 1012. The hardware/software necessary for connection to the network interface 1048 includes, for exemplary purposes only, internal and external technologies such as, modems including regular telephone grade modems, cable modems and DSL modems, ISDN adapters, and Ethernet cards.

FIG. 11 is a schematic block diagram of an example-computing environment to facilitate storing transactions in a blockchain in accordance with one or more examples described herein. FIG. 11 is a schematic block diagram of a sample-computing environment 1100 with which the subject matter of this disclosure can interact. The system 1100 includes one or more client(s) 1110. The client(s) 1110 can be hardware and/or software (e.g., threads, processes, computing devices). The system 1100 also includes one or more server(s) 1130. Thus, system 1100 can correspond to a two-tier client server model or a multi-tier model (e.g., client, middle tier server, data server), amongst other models. The server(s) 1130 can also be hardware and/or software (e.g., threads, processes, computing devices). The servers 1130 can house threads to perform transformations by employing this disclosure, for example. One possible communication between a client 1110 and a server 1130 may be in the form of a data packet transmitted between two or more computer processes.

The system 1100 includes a communication framework 1150 that can be employed to facilitate communications between the client(s) 1110 and the server(s) 1130. The client(s) 1110 are operatively connected to one or more client data store(s) 1120 that can be employed to store information local to the client(s) 1110. Similarly, the server(s) 1130 are operatively connected to one or more server data store(s) 1140 that can be employed to store information local to the servers 1130.

The above systems and methods described with respect to FIGS. 1-11 can be employed to facilitate fungal species identification in accordance with a feature extraction/learning system and in accordance with one or more examples described herein. The respective systems can be implemented on or in connection with a network of servers associated with an enterprise application, for example. In one example, the system can be associated with a cloud-based platform and can also be associated with a computing environment that comprises one or more servers and/or one or more software components that operate to perform one or more processes, one or more functions and/or one or more methodologies in accordance with the described examples. A sever as disclosed herein can include, for example, stand-alone server and/or an enterprise-class server operating a server operating system (OS) such as a MICROSOFT® OS, a UNIX® OS, a LINUX® OS, and/or another suitable server-based OS. It is to be appreciated that one or more operations performed by a server and/or one or more services provided by a server can be combined, distributed, and/or separated for a given implementation. Furthermore, one or more servers can be operated and/or maintained by a corresponding entity or different entities.

The system can be employed by various systems, such as, but not limited to server systems, electronic device systems, mobile device systems, smartphone systems, virtual machine systems, consumer service systems, mobile application systems, financial systems, digital systems, machine learning systems, artificial intelligence systems, neural network systems, network systems, computer network systems, communication systems, enterprise systems, asset management systems, cloud storage systems, and the like.

In one example, the systems described herein can be associated with a Platform-as-a-Service (PaaS). Moreover, the system and/or the components of the system can be employed to use hardware and/or software to solve problems that are technical in nature (e.g., related to a computing system, related to a server system, related to digital data processing, and so forth), that are not abstract and that cannot be performed as a set of mental acts by a human.

Systems and components can be implemented as stored software instructions that are executable by a processor to cause various operations to occur. Aspects of the systems, apparatuses or processes described herein can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), and so forth, can cause the machine(s) to perform the operations described. The systems can include memory for storing computer executable components and instructions. The systems can further include a processor (or processors) to facilitate operation of the instructions (e.g., computer executable components and instructions).

The electronic device described herein can be a computing device, a user device, a client device, a mobile device, a smart phone, a tablet device, a handheld device, a portable computing device, a smart device (e.g. an Internet-of-Things devices such as a smart television, and so forth), a wearable device, a computer, a desktop computer, a laptop computer, a point of sale (POS) device, and/or another type of electronic device associated with a display (e.g., the electronic device can be more than one of the type of devices listed above, which are non-exclusive categories in various embodiments). In an example, the interfaces described herein can render one or more graphical elements associated with the fungal images and predictions described herein and presented on a display of the electronic device. This can include management of one or more communications and/or one or more transmissions with respect to the electronic device to facilitate fungal diagnostics via the electronic device.

Networks described herein can be a communication network, a wireless network, an IP network, a voice over IP network, an internet telephony network, a mobile telecommunications network, a landline telephone network, a personal area network, a wired network, and/or another type of network. The fungal identifier component can be, for example, a stand-alone server and/or an enterprise-class server operating a server OS such as a MICROSOFT® OS, a UNIX® OS, a LINUX® OS, and/or another suitable server-based OS. It is to be appreciated that one or more operations performed by the fungal identifier component can be combined, distributed, and/or separated for a given implementation example.

It is to be noted that aspects or features of this disclosure can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the examples described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

While the subject matter has been described above in the general context of computer-executable instructions of a computer program that runs on a computer and/or computers, those skilled in the art will recognize that this disclosure also can or may be implemented in combination with other program modules. Generally, program modules include routines, programs, components, data structures, and so forth, that perform particular tasks and/or implement particular abstract data types. Moreover, those skilled in the art will appreciate that the inventive methods may be practiced with other computer system configurations, including single-processor or multiprocessor computer systems, mini-computing devices, mainframe computers, as well as personal computers, hand-held computing devices (e.g., PDA, phone), microprocessor-based or programmable consumer or industrial electronics, and the like. The illustrated aspects may also be practiced in distributed computing environments where tasks are performed by remote processing devices that are linked through a communications network. However, some, if not all aspects of this disclosure can be practiced on stand-alone computers. In a distributed computing environment, program modules may be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In another example, respective components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

Various aspects or features described herein can be implemented as a method, apparatus, system, or article of manufacture using standard programming or engineering techniques. In addition, various aspects or features disclosed in this disclosure can be realized through program modules that implement at least one or more of the methods disclosed herein, the program modules being stored in a memory and executed by at least a processor. Other combinations of hardware and software or hardware and firmware can enable or implement aspects described herein, including a disclosed method(s). The term "article of manufacture" as used herein can encompass a computer program accessible from any computer-readable device, carrier, or storage media. For example, computer readable storage media can include but are not limited to magnetic storage devices (e.g., hard disk, floppy disk, magnetic strips . . . ), optical discs (e.g., compact disc (CD), digital versatile disc (DVD), blu-ray disc (BD) . . . ), smart cards, and flash memory devices (e.g., card, stick, key drive . . . ), or the like.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or methods herein are intended to include, without being limited to including, these and any other suitable types of memory.

It is to be appreciated and understood that components, as described with regard to a particular system or method, can include the same or similar functionality as respective components (e.g., respectively named components or similarly named components) as described with regard to other systems or methods disclosed herein.

What has been described above includes examples of systems and methods that provide advantages of this disclosure. It is, of course, not possible to describe every conceivable combination of components or methods for purposes of describing this disclosure, but one of ordinary skill in the art may recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A fungal identification system, comprising:
    a memory; and
    a processor configured to execute computer instructions stored in the memory that when executed cause the system to perform operations, the computer instructions comprising:
        a learning component that comprises one or more trained models to learn pathogenic features of a given fungal species based on learning from a plurality of stored fungal species images; and
        a fungal identifier component that employs the trained models to determine pathogenic parameters of an unidentified fungal species image based on the learned pathogenic features, the fungal identifier component generates an output file that classifies the unidentified fungal species image according to the determined pathogenic parameters from the unidentified fungal species image.

2. The fungal identification system of claim 1, further comprising a database to store the plurality of fungal species images, wherein the database includes at least one of a local memory storage, a local intranet storage across a private network, and a distributed memory storage across a cloud or public network.

3. The fungal identification system of claim 1, wherein the learning component includes at least one of a neural network and an artificial intelligence classifier to learn the pathogenic parameters.

4. The fungal identification system of claim 3, wherein the neural network is implemented as at least one neuron that executes an activation function, the neuron receives weighted inputs related to image variables from the stored fungal species images and generates an output that indicates learned patterns from the respective image variables.

5. The fungal identification system of claim 4, wherein the neural network is implemented as a feed-forward network of neurons and output error terms are back propagated across the network to adjust input weighting terms to facilitate prediction accuracy of the network.

6. The fungal identification system of claim 5, further comprising an image extraction component that is employed to extract fungal features from a respective image, wherein the neural network is employed to classify the extracted fungal features.

7. The fungal identification system of claim 6, wherein the image extraction component employs convolution to extract the fungal features and generates a rectified feature map representing convolved features and rectified values having negative feature values set at about zero.

8. The fungal identification system of claim 1, wherein the fungal identifier component generates a prediction regarding an identified fungal species type and a probability output related to a confidence of the prediction.

9. The fungal identification system of claim 8, wherein the fungal identifier component further comprises a model data analyzer component that compares the prediction to a probability threshold to generate the probability output based on the probability output exceeding the probability threshold.

10. The fungal identification system of claim 1, wherein the pathogenic parameters are related to at least one of size, shape, color, and thickness of an extracted feature of the unidentified fungal species image.

11. The fungal identification system of claim 1, wherein the pathogenic parameters are related to at least one of a refractive quality, a mass spectrometry result, and an electrical/chemical reaction of the unidentified fungal species image observed in the extracted feature.

12. The computer-implemented method of claim 11, wherein the learning includes learning from at least one of a neural network and an artificial intelligence classifier to learn the pathogenic parameters.

13. The computer-implemented method of claim 12, further comprising pre-processing of the fungal species images, wherein the preprocessing includes at least one of image cropping, feature detection, matching, or rendering.

14. The computer-implemented method of claim 12, further comprising reducing learning and recognition time of the pathogenic features based on an optimization of network transmission parameters.

15. The computer-implemented method of claim 12, wherein the neural network is implemented as at least one neuron that executes an activation function, the neuron receives weighted inputs related to image variables from the stored fungal species images and generates an output that indicates learned patterns from the respective image variables.

16. The computer-implemented method of claim 15, wherein the neural network is implemented as a feed-forward network of neurons and output error terms are back propagated across the network to adjust input weighting terms to facilitate prediction accuracy of the network.

17. The computer-implemented method of claim 16, further comprising:
    extracting fungal features from a respective image; and
    classifying the extracted fungal features.

18. The computer-implemented method of claim 17, further comprising:
    employing convolution to extract the fungal features;
    generating a rectified feature map representing convolved features; and
    generating rectified values having negative feature values set at about zero.

19. A computer-implemented method, comprising:
  storing, by a system having a processor and a memory, a plurality of fungal species images;
  learning, by the system, pathogenic features of a given fungal species based on the stored fungal species images;
  determining, by the system, pathogenic parameters of an unidentified fungal species image based on the learned pathogenic features; and
  classifying, by the system, the unidentified fungal species image according to the determined pathogenic parameters from the unidentified fungal species image.

20. The computer-implemented method of claim 19, further comprising:
  generating a prediction regarding an identified fungal species type; and
  generating a probability output related to a confidence of the prediction.

21. A non-transitory machine-readable medium having machine-readable instructions that when executed by a processor cause the processor to at least:
  store a plurality of fungal species images;
  identify pathogenic features of different fungal species based on the stored fungal species images;
  determine pathogenic parameters of an unidentified fungal species image based on the identified pathogenic features; and
  classify the unidentified fungal species image according to the determined pathogenic parameters from the unidentified fungal species image.

22. The non-transitory machine-readable medium of claim 21, further comprising at least one of a neural network instruction and an artificial intelligence classifier instruction to identify the pathogenic parameters.

23. The non-transitory machine-readable medium of claim 21 further comprising wherein the instructions process the fungal images in accordance with a website, a database, a cloud, or a mobile application.

* * * * *